United States Patent
Wortzman et al.

(10) Patent No.: US 8,722,650 B1
(45) Date of Patent: *May 13, 2014

(54) EXTENDED-RELEASE MINOCYCLINE DOSAGE FORMS

(75) Inventors: Mitchell Wortzman, Scottsdale, AZ (US); R. Todd Plott, Scottsdale, AZ (US); Steven B. Newhard, Scottsdale, AZ (US); David Watt, Scottsdale, AZ (US)

(73) Assignee: Medicis Pharmaceutical Corporation, Bridgewater, NJ (US)

( * ) Notice: Subject to any disclaimer, the term of this patent is extended or adjusted under 35 U.S.C. 154(b) by 370 days.

This patent is subject to a terminal disclaimer.

(21) Appl. No.: 12/861,424

(22) Filed: Aug. 23, 2010

Related U.S. Application Data

(63) Continuation-in-part of application No. 11/166,817, filed on Jun. 24, 2005, now Pat. No. 7,919,483, which is a continuation-in-part of application No. 12/253,845, filed on Oct. 17, 2008, now Pat. No. 7,790,705, which is a continuation of application No. 11/695,513, filed on Apr. 2, 2007, now Pat. No. 8,252,776, and a continuation of application No. 11/695,514, filed on Apr. 2, 2007, now abandoned, and a continuation of application No. 11/695,541, filed on Apr. 2, 2007, application No. 12/861,424, filed on Aug. 23, 2010, which is a continuation-in-part of application No. 12/756,962, filed on Apr. 8, 2010, which is a continuation-in-part of application No. 12/536,359, filed on Aug. 5, 2009.

(60) Provisional application No. 61/235,898, filed on Aug. 21, 2009, provisional application No. 61/210,882, filed on Mar. 23, 2009, provisional application No. 61/086,728, filed on Aug. 6, 2008.

(51) Int. Cl.
*A61K 9/16* (2006.01)
*A61K 9/50* (2006.01)
*A61K 9/52* (2006.01)
*A61K 9/54* (2006.01)
*A61K 31/65* (2006.01)

(52) U.S. Cl.
USPC ........... 514/152; 424/482; 424/457; 424/458; 424/455; 424/474; 424/490; 424/495; 424/497; 424/489; 424/498

(58) Field of Classification Search
USPC ......... 424/482, 457, 458, 455, 474, 490, 497, 424/495, 489, 498; 514/152
See application file for complete search history.

(56) References Cited

U.S. PATENT DOCUMENTS

| | | |
|---|---|---|
| 3,499,959 A | 3/1970 | Corn |
| 3,932,615 A | 1/1976 | Ito et al. |
| 3,957,980 A | 5/1976 | Noseworthy |
| 3,966,922 A | 6/1976 | Okamoto et al. |
| 4,086,332 A | 4/1978 | Armstrong |
| 4,126,680 A | 11/1978 | Armstrong |
| 4,138,475 A | 2/1979 | McAinsh et al. |
| 4,369,172 A | 1/1983 | Schor et al. |
| 4,376,118 A | 3/1983 | Daher et al. |
| 4,443,442 A | 4/1984 | Skillern |
| 4,701,320 A | 10/1987 | Hasegawa et al. |
| 4,764,377 A | 8/1988 | Goodson |
| 4,792,448 A | 12/1988 | Ranade |
| 4,806,529 A | 2/1989 | Levy |
| 4,837,030 A | 6/1989 | Valorose, Jr. et al. |
| 4,925,833 A | 5/1990 | McNamara et al. |
| 4,935,411 A | 6/1990 | McNamara et al. |
| 4,935,412 A | 6/1990 | McNamara et al. |
| 4,960,913 A | 10/1990 | Szalay et al. |
| 5,007,790 A | 4/1991 | Shell |
| 5,009,895 A | 4/1991 | Lui |
| 5,122,519 A | 6/1992 | Ritter |
| 5,167,964 A | 12/1992 | Muhammad et al. |
| 5,188,836 A | 2/1993 | Muhammad et al. |
| 5,202,128 A | 4/1993 | Morella et al. |
| 5,209,978 A | 5/1993 | Kosaka et al. |
| 5,211,958 A | 5/1993 | Akkerboom et al. |
| 5,217,493 A | 6/1993 | Raad et al. |
| 5,225,916 A | 7/1993 | Kikugawa et al. |
| 5,230,895 A | 7/1993 | Czarnecki et al. |

(Continued)

FOREIGN PATENT DOCUMENTS

| | | |
|---|---|---|
| CA | 2025703 | 9/1990 |
| CA | 2068366 | 11/1992 |
| CA | 2090561 | 2/1993 |
| CN | 101658501 A | 3/2010 |
| CN | 101822650 A | 9/2010 |

(Continued)

OTHER PUBLICATIONS

U.S. Appl. No. 61/235,898, filed Aug. 21, 2009, Wortzman, et al.
U.S. Appl. No. 61/210,882, filed Mar. 23, 2009, Wortzman, et al.
U.S. Appl. No. 61/086,728, filed Aug. 6, 2008, Wortzman, et al.
AAI International Procore® Technology, referencing patents issued prior to 2000.

(Continued)

*Primary Examiner* — Savitha Rao
(74) *Attorney, Agent, or Firm* — Toan P. Vo; Timothy J. Shea, Jr.; Matthew S. Bodenstein

(57) ABSTRACT

An oral dosage form has the following: an amount of minocycline selected from the group consisting of 55 mg, 80 mg, and 105 mg; an amount of lactose monohydrate; an amount of hydroxypropylmethylcellulose. The hydroxypropylmethylcellulose is at least 8.3 to about 9.8% hydroxypropoxylated. The minocycline in the oral dosage form has a dissolution profile or release rates about 35% to about 50% in 1 hour, about 60% to about 75% in 2 hours, and at least about 90% in 4 hours. There is also provided a method of treating acne in a human and a method of assisting a physician in prescribing a dose of minocycline for the treatment of acne.

10 Claims, No Drawings

(56) References Cited

U.S. PATENT DOCUMENTS

| | | | |
|---|---|---|---|
| 5,262,173 A | 11/1993 | Sheth et al. | |
| 5,277,916 A | 1/1994 | Dwyer et al. | |
| 5,283,065 A | 2/1994 | Doyon et al. | |
| 5,300,304 A | 4/1994 | Sheth et al. | |
| 5,324,751 A | 6/1994 | DuRoss | |
| 5,348,748 A | 9/1994 | Sheth et al. | |
| 5,413,777 A | 5/1995 | Sheth et al. | |
| 5,459,135 A | 10/1995 | Golub et al. | |
| 5,518,730 A | 5/1996 | Fuisz | |
| 5,554,654 A | 9/1996 | Yu et al. | |
| 5,582,837 A | 12/1996 | Shell | |
| 5,665,776 A | 9/1997 | Yu et al. | |
| 5,674,539 A | 10/1997 | Tomas | |
| 5,698,593 A | 12/1997 | Peck | |
| 5,776,489 A | 7/1998 | Preston et al. | |
| 5,780,049 A | 7/1998 | Deckner et al. | |
| 5,783,212 A | 7/1998 | Fassihi et al. | |
| 5,789,395 A | 8/1998 | Amin et al. | |
| 5,800,836 A | 9/1998 | Morella et al. | |
| 5,814,331 A | 9/1998 | Holen | |
| 5,824,343 A | 10/1998 | Ng et al. | |
| 5,834,450 A | 11/1998 | Su | |
| 5,855,904 A | 1/1999 | Chung et al. | |
| 5,908,838 A | 6/1999 | Gans | |
| 5,972,389 A | 10/1999 | Shell et al. | |
| 6,015,804 A | 1/2000 | Golub et al. | |
| 6,087,382 A | 7/2000 | Bonner, Jr. et al. | |
| 6,120,803 A | 9/2000 | Wong et al. | |
| 6,165,513 A | 12/2000 | Dansereau et al. | |
| 6,165,999 A | 12/2000 | Vu | |
| 6,194,000 B1 | 2/2001 | Smith et al. | |
| 6,340,475 B2 | 1/2002 | Shell et al. | |
| 6,340,476 B1 | 1/2002 | Midha et al. | |
| 6,429,204 B1 | 8/2002 | Golub et al. | |
| 6,455,583 B1 | 9/2002 | Pflugfelder et al. | |
| 6,497,902 B1 | 12/2002 | Ma | |
| 6,585,997 B2 | 7/2003 | Moro et al. | |
| 6,638,922 B2 | 10/2003 | Ashley et al. | |
| 6,667,060 B1 | 12/2003 | Vandecruys et al. | |
| 6,673,843 B2 | 1/2004 | Arbiser | |
| 6,863,830 B1 | 3/2005 | Purdy et al. | |
| 6,958,161 B2 | 10/2005 | Hayes et al. | |
| 7,008,631 B2 | 3/2006 | Ashley | |
| 7,063,862 B2 | 6/2006 | Lin et al. | |
| 7,211,267 B2 | 5/2007 | Ashley | |
| 7,541,347 B2 | 6/2009 | Wortzman et al. | 514/152 |
| 7,544,373 B2 | 6/2009 | Wortzman et al. | |
| 7,790,705 B2 | 9/2010 | Wortzman et al. | |
| 7,919,483 B2 | 4/2011 | Wortzman et al. | |
| 7,976,870 B2 | 7/2011 | Berner et al. | |
| 2002/0015731 A1 | 2/2002 | Appel et al. | |
| 2002/0044968 A1 | 4/2002 | van Lengerich | |
| 2003/0044446 A1 | 3/2003 | Moro et al. | |
| 2003/0082120 A1 | 5/2003 | Milstein | |
| 2003/0130240 A1 | 7/2003 | Ashley | |
| 2003/0139380 A1 | 7/2003 | Ashley | |
| 2003/0199480 A1 | 10/2003 | Hayes et al. | |
| 2003/0229055 A1 | 12/2003 | Ashley | |
| 2004/0002481 A1 | 1/2004 | Ashley et al. | |
| 2004/0037789 A1 | 2/2004 | Moneuze et al. | |
| 2004/0115261 A1 | 6/2004 | Ashley | |
| 2004/0127471 A1 | 7/2004 | Reisberg | |
| 2004/0185105 A1 | 9/2004 | Berner et al. | |
| 2004/0228912 A1 | 11/2004 | Chang et al. | |
| 2005/0136107 A1 | 6/2005 | Patel et al. | |
| 2005/0148552 A1 | 7/2005 | Ryan et al. | |
| 2006/0293290 A1 | 12/2006 | Wortzman et al. | |
| 2007/0154547 A1 | 7/2007 | Flanner et al. | |
| 2007/0254855 A1 | 11/2007 | Wortzman et al. | |
| 2007/0259039 A1 | 11/2007 | Wortzman et al. | |
| 2007/0270390 A1 | 11/2007 | Wortzman et al. | |
| 2007/0275933 A1 | 11/2007 | Wortzman et al. | |
| 2008/0070872 A1 | 3/2008 | Wortzman et al. | |
| 2008/0161273 A1 | 7/2008 | Arsonnaud et al. | |
| 2008/0241197 A1 | 10/2008 | Wortzman et al. | |
| 2008/0241235 A1 | 10/2008 | Wortzman et al. | |
| 2008/0241236 A1 | 10/2008 | Wortzman et al. | |
| 2008/0241241 A1 | 10/2008 | Wortzman et al. | |
| 2008/0242641 A1 | 10/2008 | Wortzman et al. | |
| 2008/0242642 A1 | 10/2008 | Wortzman et al. | |
| 2008/0260824 A1 | 10/2008 | Nangia et al. | |
| 2008/0318910 A1 | 12/2008 | Desjardins et al. | |
| 2010/0035846 A1 | 2/2010 | Wortzman et al. | |
| 2010/0215744 A1 | 8/2010 | Watt et al. | |
| 2010/0330131 A1 | 12/2010 | Wortzman et al. | |
| 2012/0002892 A1 | 1/2012 | Eichhorn et al. | |

FOREIGN PATENT DOCUMENTS

| | | |
|---|---|---|
| CN | 101836961 A | 9/2010 |
| EP | 0184389 | 6/1986 |
| EP | 0418565 | 3/1991 |
| EP | 0558913 | 9/1992 |
| GB | 2414668 | 12/2005 |
| GB | 2 420 708 A | 6/2006 |
| JP | 020064374 A | 1/1990 |
| JP | 2001-278781 A | 10/2001 |
| JP | 2002-509887 A | 4/2002 |
| JP | 2004-224754 A | 8/2004 |
| WO | WO 93/18755 | 9/1993 |
| WO | WO 98/11879 | 3/1998 |
| WO | WO 98/55107 | 12/1998 |
| WO | WO 99/49868 A1 | 10/1999 |
| WO | WO 99/58131 | 11/1999 |
| WO | WO 02/080932 | 10/2002 |
| WO | WO 03/088906 | 10/2003 |
| WO | WO 2004/012700 | 2/2004 |
| WO | WO 2004/078111 A2 | 9/2004 |
| WO | WO 2004/091483 A2 | 10/2004 |
| WO | WO 2007/038867 A1 | 4/2007 |
| WO | WO 2007/102447 A1 | 9/2007 |
| WO | WO 2008/102161 A2 | 8/2008 |
| WO | WO 2010/033800 A2 | 3/2010 |
| WO | WO 2010/046932 A2 | 4/2010 |

OTHER PUBLICATIONS

AAI International Proslo™ and Proslo™ II Tablets Technology, referencing patents issued prior to 2000.

AAI International Prosorbo® Technology, referencing patents issued prior to 2000.

American Hospital Formulary Service Drug Information 88, 1988, pp. 330-331.

A Comparison of the Side Effects Produced by Vectrin and Dynacin After Normal Dosage. Clinical Acne Reviews, vol. 2 Oct. 1977.

Drugs.com, Drug information online, Minocin PAC product information, Aug. 2007.

International Search Report and Written Opinion dated Feb. 26, 2007, for PCT/US06/23761.

International Search Report and Written Opinion mailed Dec. 5, 2007 pp. 1-18.

Is minocycline overused in acne?, Drug and Therapeutics Bulletin. vol. 44 No. 8, 60-62, Aug. 2006.

Minocin Product Insert, Wyeth Pharmaceuticals Inc. Rev 10/05.

Prescribingreference.com, Prescribing Reference, Drug News—Minocin PAC for Acne (Oct. 11, 2006).

MinoPAC product information, Monthly prescribing Reference (Oct. 2006) and the product information (Aug. 2007).

Physician's Desk Reference; Minocin®: Minocycline Hydrochloride for Oral Use; Physician's Desk Reference, 1989, pp. 1134-1136, 43rd Edition; Edward R. Barnhard, publisher, Medical Economics Co., Inc.; Oradell, NJ.

Solodyn (Minocycline HCl Extended Release Tablets) Labeling and package insert information, submitted with a New Drug Application approved May 8, 2006.

Office Communication dated Nov. 6, 2007 in U.S. Appl. No. 11/166,817.

Office Communication dated Nov. 13, 2008 in U.S. Appl. No. 11/166,817.

Office Communication dated Nov. 6, 2007 in U.S. Appl. No. 11/776,669.

(56) References Cited

OTHER PUBLICATIONS

Office Communication dated Jun. 17, 2008 in U.S. Appl. No. 11/776,669.
Office Communication dated Dec. 1, 2008 in U.S. Appl. No. 11/776,669.
Office Communication dated Nov. 6, 2007 in U.S. Appl. No. 11/776,676.
Office Communication dated Aug. 8, 2008 in U.S. Appl. No. 11/776,676.
Office Communication dated Nov. 6, 2007 in U.S. Appl. No. 11/776,711.
Office Communication dated Jun. 17, 2008 in U.S. Appl. No. 11/776,711.
Office Communication dated Nov. 17, 2008 in U.S. Appl. No. 11/944,186.
Office Communication dated Dec. 24, 2008 in U.S. Appl. No. 11/695,514.
Office Communication dated Jul. 22, 2008 in U.S. Appl. No. 11/695,528.
Office Communication dated Jul. 23, 2008 in U.S. Appl. No. 11/695,539.
Office Communication dated Dec. 23, 2008 in U.S. Appl. No. 11/695,539.
Akamatsu, et al., "Effect of Doxycycline on the Generation of Reactive Oxygen Species: A Possible Mechanism of Action of Acne Therapy with Doxycycline"; Acta Derm Venereol (Stockh), 1992; 72:178-179.
Akamatsu, et al., "Effects of subminimal inhibitory concentrations of minocycline on neutrophil chemotactic factor production in comedonal bacteria, neutrophil phagocytosis and oxygen metabolism", Archives of Dermatological Research, vol. 283, 1991, pp. 524-528.
Arndt et al., "What disorders present with inflamed skin?" Cutaneous Medicine and Surgery, An Intergrated Program in Dermatology, vol. 1, pp. 470-471, 1996.
Arnold et al., Andrews' Diseases of the Skin: Clinical Dermatology, 8th Edition, p. 254, 1990.
Bikowski, "Treatment of Rosacea With Doxycycline Monohydrate", Therapeutics for the clinician, vol. 66, Aug. 2000, pp. 149-152.
Brown, et al., "Diagnosis and Treatment of Ocular Rosacea", Official Journal of American Academy of Ophthalmology, vol. 85, Aug. 1978, pp. 779-786.
Champion et al., "Disorders of the Sebaceous Glands," Textbook of Dermatology, 6th Edition, vol. 3, pp. 1958-1961, 1998.
Darrah, et al., "An open multicentre study to compare fusidic acid lotion and oral minocycline in the treatment of mild-to-moderate acne vulgaris of the face", European Journal of Clinical Research, 1996, vol. 8, pp. 97-107.
James Q. Del Rosso, Clinical Significance of Brand Versus Generic Formulations: Focus on Oral Minocycline, Cutis, vol. 77, 153-156, Mar. 2006.
James Q. Del Rosso, et al. Weight-based Dosing of a Novel Antibiotic for Moderate-to-Severe Acne Vulgaris Offers Potential for Improved Safety and Tolerability, www.millennium.com/ao/acne, Millennium CME Institute, Inc., 2006.
Dreno, et al., "Multicenter Randomized Comparative Double-Blind Controlled Clinical Trial of the Safety and Efficacy of Zinc Gluconate versus Minocyclin Hydrochloride in the Treatment of Inflammatory Acne vulgaris", Dermatology, 2001, vol. 203, pp. 135-140.
Adolfo C. Fernandez-Obregon, Azithromycin for the treatment of acne, International Journal of Dermatology 2000, 39, 45-50.
Barbara Fingleton, CMT-3 CollaGenex, Current Opinion in Investigational Drugs, vol. 4, No. 12, 1460-1467, Dec. 2003.
Fleischer, A.B. et al. Safety and Efficacy of a New Extended-Release Formulation of Minocycline. Cutis 2006; 78 (suppl 4):21-31.
Freedberg, et al., Fizpatrick's Dermatology in General Medicine, 5th Edition, vol. 1, pp. 77-78, 1999.
Freeman, et al., "Therapeutic Focus Minocycline in the treatment of acne", BJCP, Mar. 1989, vol. 43, pp. 112-114.
Gans et al. The Solubility and Complexing properties of Oxytetracycline and Tetracycline II, Journal of the American Pharmaceutical Association, Sci. Ed. 46, No. 10, Oct. 1957.
K. J. Gardner, et al., Comparison of serum antibiotic levels in acne patients receiving the standard or a modified release formulation of minocycline hydrochloride. Clinical and Experimental Dermatology, vol. 22, pp. 72-76, Jan. 1997.
Garner SE, et al., "Minocycline for acne vulgaris: efficacy and safety", (Cochrane Review), The Cochrane Library, issue 1, 2004, Chichester, UK: John Wiley & Sons, Ltd.
Gollnick, Harald, et al., "Management of Acne, A Report From a Global Alliance to Improve Outcomes in Acne", Supplement to Journal of the American Academy of Dermatology, Jul. 2003, vol. 49, No. 1, S1-38.
Golub, et al., "Tetracyclines Inhibit Connective Tissue Breakdown: New Therapeutic Implications for an Old Family of Drugs", Critical Reviews in Oral Biology and Medicine, vol. 2, No. 2, 1991, pp. 297-322.
Aditya K. Gupta et al., Solodyn (Minocycline HCl, USP) Extended-Release Tablets, LE JACQ, 291-292, Nov. Dec. 2006.
Harrison, "A comparison of doxycycline and minocycline in the treatment of acne vulgaris", Clinical and Experimental Dermatology, 1998, vol. 13, pp. 242-244.
Hersle, et al., "Minocycline in Acne Vulgaris: a Double-Blind Study", Current Therapeutic Research, Mar. 1976, vol. 19, No. 3, pp. 339-342.
Charles G. Hubbell et al. Efficacy of Minocycline Compared with Tetracycline in Treatment of Acne Vulgaris, Archives of Dermatology, vol. 118, pp. 989-992, Dec. 1982.
Illig, "Positive Side Effects of Antibiotic and Antimicrobial Substances in Therapy", Infection, vol. 7, Suppl. 6, 1979, pp. S 584-588. (with English-language translation).
Muzharul M. Islam, A Nonantibiotic Chemically Modified Tetracycline (CMT-3) Inhibits intimal Thickening, American Journal of Pathology; vol. 163, No. 4, 1557-1566, Oct. 2003.
Jonas, et al., "Minocycline", Therapeutic Drug Monitoring, vol. 4, 1982, pp. 137-145.
Kelly, et al., "Metabolism and Tissue Distribution of Radiosotopically Labeled Minocycline", Elsevier Toxicology and Applied Pharmacology, 1967, vol. 11, pp. 171-183.
Leyden, J. Introduction. Cutis 2006; 78 (suppl 4):4-5.
Leyden, James J., "Absorption of minocycline hydrochloride and tetracycline hydrochloride", J. Am. Acad. Dermatol. 12:308-312, 1985.
Leyden, James J., et al., "The antimicrobial effects in vivo of minocycline, doxycycline and tetracycline in humans", The Journal of Dermatological Treatment, Dec. 1996, vol. 7, No. 4, 223-225.
Leyden, James J., et al., "Clinical Considerations in the Treatment of Acne Vulgaris and Other Inflammatory Skin Disorders: Focus on Antibiotic Resistance", Cutis 2007 (suppl. 6), vol. 79, No. 65, 9-25.
Leyden, James J., et al., "Comparison of Tazarotene and Minocycline Maintenance Therapies in Acne Vulgaris", Archives of Dermatology, May 2006, 605-612.
Leyden, et al. 2006. New Extended-Release Minocycline. First Systemic Antibiotic Approved for the Treatment of Acne. A Supplement to Cutis, 78(4S): 1-32.
Leyden, James J., et al., "*Pseudomonas aeruginosa* Gram-Negative Folliculitis", Archives of Dermatology, 1979, vol. 115, 1203-1204.
Leyden, James J., et al., "Tetracycline and Minocycline Treatment, Effects on Skin-Surface Lipid Levels and Propionibacterium acnes", Archives of Dermatology, 1982, vol. 118, 19-22.
Jing Li et al., Evidence for Dissolution Rate-Limited Absorption of COL-3, a Matrix Metalloproteinase Inhibitor, Leading to the Irregular Absorption Profile in Rats after Oral Administration, Pharmaceutical Research, Vo. 19, No. 11, 1655-1662, Nov. 2002.
Bal L. Lokeshwar et al., Inhibition of Cell Proliferation, Invasion, Tumor Growth and Metastasis by an Oral Non-Antimicrobial Tetracycline Analog (COL-3) in a Metastatic Prostate Cancer Model, International Journal of Cancer: 98, 297-309 (2002).
Marks, Ronald, et al., (eds.) "Dermatologic Therapy in Current Practice", Chapter 3, 35-44 (2002).

(56) References Cited

OTHER PUBLICATIONS

Millar, et al., "A general practice study investigating the effect of minocycline (Minocin) 50 mg bd for 12 weeks in the treatment of acne vulgaris", The British Journal of Clinical Practice, Aug. 1987, vol. 41, No. 8, pp. 882-886.
Millar, MB, ChB., et al., "A general practice study investigating the effect of minocycline (Minocin) 50 mg bd for 12 weeks in the treatment of acne vulgaris", British Journal of Clinical Practice, vol. 41, No. 8, Aug. 1987, pp. 882-886.
Falk Ochsendorf, Systemic antibiotic therapy of acne vulgaris, Journal der Deutschen Dermatologischen Gesellschaft, 4:828-841, 2006.
Piérard-Franchimont, et al. 2002. Lymecycline and Minocycline in Inflammatory Acne. Skin Pharmacol Appl Skin Physiol, 15:112-119.
Gilbert Plott, Extended-Release Minocycline: Is Efficacy Dose-dependent in the Approved Dose Range?, Poster Presentation for the Dusa Pharmaceuticals, Inc. Medical Conferences and Trade Shows, Hawaii, Mar. 3-9, 2007.
Plott, R. T. and Wortzman, M. Key Bioavailability Features of a New Extended-Release Formulation of Minocycline Hydrochloride Tablets. Cutis 2006; 78 (suppl 4):6-10.
Allen N. Sapadin et al., Tetracyclines: Nonantibiotic properties and their clinical implications, American Academy of Dermatology, Inc., 258-265, Feb. 2006.
Richard E. B. Seftor et al, Chemically modified tetracyclines inhibit human melanoma cell invasion and metastasis, Clinical & Experimental Metastasis, vol. 16, No. 3, 217-225 (1998).
Sheehan-Dare, et al "Double-blind Comparison of Topical Clindamycin and Oral Minocycline in the Treatment of Acne Vulgaris", Acta Derm Venereol (Stockh), 70, pp. 534-537, 1990.
Smit, "Minocycline versus Doxycycline in the Treatment of Acne vulgaris", Dermatologica, vol. 157, 1978, pp. 186-190.
Smith, Kelly, et al., "Safety of Doxycycline and Minocycline: A Systematic Review", Clinical Therapeutics, The International Peer-Reviewed Journal of Drug Therapy, vol. 27, No. 9, Sep. 2005, 1329-1342.
Stewart, D.M. et al. Dose Ranging Efficacy of New Once-Daily Extended-Release Minocycline for Acne Vulgaris. Cutis 2006; 78 (suppl 4):11-20.
Ta et al., Effects of Minocycline on the Ocular Flora of Patients with Acne Rosacea or Seborrheic Blepharitis, Cornea vol. 22(6): 545-548, 2003.
Schach Von Wittenau, et al., The Distribution of Tetracyclines in Tissues of Dogs After Repeated Oral Administration, The Journal of Pharmacology and Experimental Therapeutics, 1965, vol. 152, No. 1, pp. 164-169.
Webster, "Inflammation in acne vulgaris", Journal of the American Academy of Dermatology, vol. 33, No. 2, part 1, Aug. 1995, pp. 247-253.
Webster, et al., "Suppression of Polymorphonuclear Leukocyte Chemotactic Factor Production in Propionibacterium acnes by Subminimal Inhibitory Concentrations of Tetracycline, Ampicillin, Minocycline, and Erythromycin", Antimicrobial Agents and Chemotherapy, vol. 21, No. 5, May 1982, pp. 770-772.
Williams D. N., et al., "Minocycline: Possible vestibular side-effects. Lancet. Sep. 28, 1974;2(7883):744-6.
Office Communication dated May 29, 2009 in U.S. Appl. No. 11/944,186.
Office Communication dated May 29, 2009 in U.S. Appl. No. 11/776,711.
Agwuh, K.N., et al., "Pharmacokinetics of the tetracyclines including glycylcyclines," J. Antimicrobial Chemotherapy vol. 58, 256-265 (Jul. 1, 2006).
American Hospital Formulary Service, AHFS Drug Information 446-448 (2003).
Cartwright, A.C., et al., "A comparison of the bioavailability of minocycline capsules and film-coated tablets," J. Antimicrobial Chemotherapy vol. 1, 317:322 (1975).
Cullen, S.I., et al., "Minocycline therapy in acne vulgaris", Cutis vol. 17, No. 6, 1208-1214 (1976).

Del Rosso, J.Q., "A status report on the use of subantimicrobial-dose doxycycline: a review of the biologic and antimicrobial effects of the tetracyclines," Cutis 118-122 (Jun. 1, 2004).
Del Rosso, J.Q., "What's new in the Medicine Cabinet?", Supplement to the Feb. 2005 Skin and Aging Conference, pp. 3-6.
dePaz, S., et al., "Severe hypersensitivity reaction to minocycline", Invest. Allergol. Clin. Immunol., vol. 9, No. 6, 403-404 (1999).
Eady, A.E., et al., "Is antibiotic resistance in cutaneous propionibacteria clinically relevant?", Amer. J. Clin. Dermatol., vol. 4, No. 12, 813-831 (2003).
Goldstein, N.S., et al., "Minocycline as a cause of drug-induced autoimmune hepatitis", Amer. J. Clin. Pathol., vol. 114, 591-598 (2000).
Gump, D.W., et al., "Side effects of minocycline: different dosage regimens," Antimicrobial Agents and Chemotherapy, vol. 12, No. 5, 642-646 (Nov. 1977).
Healy, N., et al., "Fortnightly review, acne," BMJ vol. 308, 831-833 (1994).
Johnson, B.A., et al., "Use of systemic agents in the treatment of acne vulgaris," Am. Fam Physician vol. 62,1823-1830, 1835-1836 (Oct. 15, 2000).
Lawrenson, R.A., et al., "Liver damage associated with minocycline use in acne", Drug Safety, vol. 23, No. 4, 333-349 (2000).
MacDonald, H., et al., "Pharmacokinetic studies on minocycline in man," American Cyanamid (Lederle Laboratories division) 852-861 (1973).
Shalita, A., "The integral role of topical and oral retinoids in the early treatment of acne," J. European Acad. Derm. Venereol. vol. 15, Suppl. 3, 43-49 (2001).
Office Communication dated Jun. 10, 2009 in U.S. Appl. No. 11/776,676.
Office Communication dated Jun. 10, 2009 in U.S. Appl. No. 11/695,514.
Office Communication dated Jun. 25, 2009 in U.S. Appl. No. 11/776,669.
Office Communication dated Nov. 6,2009 in Chinese Pat. App. Ser. No. 2006800224203 (with English translation).
Yang, Jian, et al., LingNan Skin Disease Magazine, No. 1, p. 38 (1994) (with English translation).
Extended European Search Report in European Application No. 06773507.6, dated Jul. 1, 2009.
Examination Report in NZ Application No. 564093; dated Oct. 29, 2009.
Office Communication dated Mar. 31, 2010 in U.S. Appl. No. 11/776,669.
Office Communication dated Mar. 31, 2010 in U.S. Appl. No. 11/776,676.
Office Communication dated Mar. 31, 2010 in U.S. Appl. No. 11/776,711.
Office Communication dated Apr. 2, 2010 in U.S. Appl. No. 11/944,186.
"Minocycline Hydrochloride Capsules, USP Bioequivalence Study", Warner Chilcott.
Anlar, et al., "Physico-chemical and bioadhesive properties of polyacrylic acid polymers," *Pharmazie* 48(4):285-287, Abstract, Verlag Pharmazautischer Verlag, Germany (1993).
Cohen, P.M., "A General Practice Study Investigating the Effect of Minocin 50 mg b.d. For 12 Weeks in the Treatment of Acne Vulgaris," J. Int. Med. Res. 13:214-221, Cambridge Medical Publications, England (1985).
Coskey, R.J., "Acne: Treatment with Minocyclinc," *Therapeutics for the Clinician* 17:799-801 , CUTIS, United States (1976).
Cullen, S.I., "Low-Dose Minocycline Therapy in Tetracycline-Recalcitrant Acne Vulgaris," *Therapeutics for the Clinician* 21:101-105, CUTIS, United States (1978).
Del Rosso, et al., "Optimizing Use of Oral Antibiotics in Acne Vulgaris," *Dermatologic. clinics*. 27: 33-42, Elsevier Health Sciences Division, United States (2009).
Del Rosso, et al., "Current Approach to Acne Management: A Community-Based Analysis," *Cutaneous Medicine for the Practitioner* 83(6S):5-24, Quadrant HealthCom, United States (2009).

(56) References Cited

OTHER PUBLICATIONS

Elkayam, O., et al., "Minocycline-Induced Autoimmune Syndromes: An Overview," *Seminars in Arthritis and Rheumatism* 28(6):392-397, Stratton, United States (1999).

Gao, P., et al., "Swelling of Hydroxypropyl Methylcelluose Matrix Tablets. 2. Mechanistic Study of the Influence of Formulation Variables on Matrix Performance and Drug Release," *Journal of Pharmaceutical Sciences* 85(7):732-740, American Chemical Society and American Pharmaceutical Association, United States (1996).

Greco, T.P., et al., "Minocycline Toxicity: Experience with an Altered Dosage Regimen," *Current Therapeutic Research* 25(2):193, Therapeutic Research Press, Inc., United States (1979).

Nayak, et al., "Gastroretentive drug delivery systems: a review," *Asian Journal of Pharmaceutical and Clinical Research*, 3(1):2-10, Elsevier, United States (2010).

Samani, S. M., et al., "The effect of polymer blends on release profiles of diclofenac sodium from matrices," *European Journal of Pharmaceuticals and Biopharmaceuticals* 55(3):351-355, Elsevier Science B.V., Netherlands (2003).

Torok, et al., "Long-Term Safety of a Modified-Release Formulation of Minocycline for Treating Moderate to Severe Acne," program and abstracts of the Foundation of Research and Education in Dermatology Winter Clinical Dermatology Conference; Mar. 14-18, 2008, Kapalua, Hawaii, 9 pages.

"Bioadhesion," Lubrizol Pharmaceutical Bulletin 23:1-20, Edition: Oct. 29, 2008, The Lubrizol Corporation, United States (2008).

"Carbopol and its Applications in pharmaceutical dosage forms," accessed at www.pharmainfo.net, submitted Oct. 27, 2007, 6 pages.

"Carbopol Polymers for Pharmaceutical Drug Delivery Applications," accessed at http://www.drugdeliverytech.com/Main/Back-Issues/345.aspx, available online Sep. 27, 2008, 3 pages.

Opadry II Brochure, 1990, 3 pages.

Physician's Desk Reference®, 51st Ed., Minocin® Minocycline Hydrochloride Pellet-Filled Capsules, Thomson PDR, Montvale, New Jersey, pp. 1429-1431 (1997).

The 2002 Physician's Desk Reference, 56th Ed., MMINOCIN®, Minocycline Hydrochloride Pellet-Filled Capsules, Thomson PDR, Montvale, New Jersey, pp. 1864-1865 (2002).

Unites States Pharmacopeia: Dissolution test described in US Pharmacopoeia XXIII, <724> Drug Release: Extended-release Articles-General Drug Release Standard, USP 23:1793, USP, United States (1995).

International Preliminary Report on Patentability for International Application No. PCT/US2007/008086, United States Patent Office, United States, mailed on Feb. 2, 2011.

International Search Report and Written Opinion for International Application No. PCT/US2009/052873, United States Patent Office, United States, mailed Oct. 1, 2009.

International Preliminary Report on Patentability for International Application No. PCT/US2009/052873, United States Patent Office, United States, mailed Oct. 4, 2010.

Office Action mailed Nov. 17, 2009, in U.S. Appl. No. 12/253,845, inventors Wortzman el al., filed Oct. 17, 2008.

Office Action mailed Mar. 4, 2010, in U.S. Appl. No. 12/253,845, inventors Wortzman et al., filed Oct. 17, 2008.

Office Action mailed Oct. 18, 2011, in U.S. Appl. No. 12/536,359, inventors Wortzman et al., filed Aug. 5, 2009.

Office Action mailed Aug. 4, 2010, in U.S. Appl. No. 12/253,845, inventors Wortzman et al., filed Oct. 17, 2008.

Office Action mailed Nov. 6, 2007, in U.S. Appl. No. 11/166,817, inventors Wortzman et al., filed Jun. 24, 2005.

Office Action mailed Nov. 13, 2008, in U.S. Appl. No. 11/166,817, inventors Wortzman et al., filed Jun. 24, 2005.

Office Action mailed Mar. 7, 2011, in U.S. Appl. No. 11/695, 513, inventors Wortzman et al., filed Apr. 2, 2007.

Office Action mailed Oct. 25, 2011, in U.S. Appl. No. 11/695,513, inventors Wortzman et al., filed Apr. 2, 2007.

Office Action mailed Jul. 22, 2008, in U.S. Appl. No. 11/695,528, inventors Wortzman et al., filed Apr. 2, 2007.

Office Action mailed Dec. 23, 2008, in U.S. Appl. No. 11/695,528, inventors Wortzman et al., filed Apr. 2, 2007.

Office Action mailed Jul. 23, 2008, in U.S. Appl. No. 11/695,539, inventors Wortzman et al., filed Apr. 2, 2007.

Office Action mailed May 24, 2011, in U.S. Appl. No. 12/875,876, inventors Wortzman et al., filed Sep. 3, 2010.

Office Action mailed Jun. 1, 2012, in U.S. Appl. No. 12/536,359, inventors Wortzman et al., filed Aug. 5, 2009.

Del Rosso, et al., "Recently Approved Systemic Therapies for Acne Vulgaris and Rosacea," *Drug Therapy Topics*, vol. 80, Aug. 2007, p. 113-120.

Fanning, et al., "Distressing Side-Effects of Minocycline Hydrochloride," *Arch. Intern. Med.*, vol. 136, pp. 761-762 (1976).

Gould, et al., "Minocycline Therapy," *Arch. Otolaryngol.*, vol. 96, p. 291 (1972).

Mahaguna, et al., "Influence of hydroxypropyl methylcellulose polymer on in vitro and in vivo performance of controlled release tablets containing alprazolam," *European Journal of Pharmaceutics and Biopharmaceutics*, vol. 56, pp. 461-468 (2003).

Shah, et al., "In vitro Dissolution Profile Comparison—Statistics and Analysis of the Similarity Factor, $f_2$," *Pharmaceutical Research*, vol. 15, No. 6, pp. 889-896 (1998).

Office Action mailed Dec. 10, 2012, in U.S. Appl. No. 12/756,962, inventors Watt et al., filed Apr. 8, 2010.

EXTENDED-RELEASE MINOCYCLINE DOSAGE FORMS

CROSS-REFERENCE TO RELATED APPLICATIONS

The present application claims priority based on U.S. Provisional Application No. 61/235,898, filed Aug. 21, 2009. The present application is also a continuation-in-part of U.S. Ser. No. 11/166,817, filed Jun. 24, 2005 now U.S. Pat. No. 7,919,483. The present application is a continuation-in-part of U.S. Ser. No. 12/253,845, filed Oct. 17, 2008 now U.S. Pat. No. 7,790,705, which is a continuation of U.S. Ser. Nos. 11/695,513 now U.S. Pat. No. 8,252,776, 11/695,514 now abandoned, and 11/695,541, all filed Apr. 2, 2007. The present application is also a continuation-in-part application of U.S. Ser. No. 12/756,962, filed Apr. 8, 2010, which is also a continuation-in-part application of U.S. Ser. No. 12/536,359, filed Aug. 5, 2009, which claims priority based on U.S. Provisional Applications 61/210,882, filed Mar. 23, 2009, and 61/086,728, filed Aug. 6, 2008.

BACKGROUND OF THE DISCLOSURE

1. Field of the Disclosure

The present disclosure relates to extended-release, minocycline oral dosage forms. The present disclosure further relates to a method for treating acne in a human. The present disclosure further relates to a method for assisting a physician in prescribing a dose of minocycline for the treatment of acne.

2. Description of the Related Art

Acne affects large patient populations, and is a common inflammatory skin disorder that usually localizes in sebaceous areas of the body, including on the face, back and chest.

Oral tetracycline-class antibiotics are frequently used in the treatment of acne. One oral tetracycline-class antibiotic used in the treatment of acne is minocycline hydrochloride. Oral dosage forms of minocycline hydrochloride are available commercially under various trade names.

Tetracycline-class antibiotics including minocycline hydrochloride are known to have side effects. These side effects include vestibular side effects or symptoms such as vertigo, dizziness or blurred vision. These effects are sometimes disabling. See, Gould & Brookler, Arch. Otolarang. Vol. 96, p. 291 (1972); Williams et al., Lancet, Sep. 28, 1974, p. 144-45; Fanning & Gump, Arch. Intern. Med., Vol. 136, pp. 761-62 (1976). Headache and general malaise, along with gastrointestinal symptoms such as the diarrhea, nausea, gas, or cramps, may also occur. Dry nose and dry mouth are also occasionally encountered.

Optimizing effective dosage amount of minocycline hydrochloride balanced with managing of adverse side effects in acne patients has been hampered by limited commercial availability of different strengths of dosage forms. Related applications of the assignee of the present application have disclosed the use of dosages of minocycline hydrochloride at 45 mg, 65 mg, 90 mg, 115 mg, and 135 mg. These related applications are discussed in U.S. Ser. Nos. 11/166,817; 11/695,513; 11,695,541; 11/695,514; 12/253,845; 12/536,359; and 12/756,962 as noted above.

There exists a need for dosage forms of different strengths of minocycline hydrochloride that provide the desired extended release profile without undue side effects and also provide for more targeted dosing of 1 mg/kg/day.

SUMMARY OF THE DISCLOSURE

The present disclosure provides three dosage forms in which the amount of minocycline is 55 mg, 80 mg, and 105 mg.

The present disclosure also provides that each of the three dosage forms has a vehicle that includes a fast dissolving carrier and an amount of hydroxypropylmethylcellulose.

The present disclosure further provides that the hydroxypropylmethylcellulose is 8.3-9.8% hydroxypropoxylated so that the minocycline in the oral dosage form achieves a desired release rate or dissolution of about 35% to about 50% in 1 hour, about 60% to about 75% in 2 hours, and at least about 90% in 4 hours. The dosage form preferably achieves a dissolution of 35% to 50% in 1 hour, 60% to 75% in 2 hours, and at least 90% in 4 hours.

The present disclosure still further provides a method of treating acne in a human including the step of administering to the person once per day an oral dosing form having an amount of minocycline selected from the group consisting of 55 mg, 80 mg, and 105 mg in a vehicle with a fast dissolving carrier and an amount of hydroxypropylmethylcellulose that is 8.3-9.8% hydroxypropoxylated. Thus, each dosage form can be manufactured in mass and achieve the desired release rates of about 35% to about 50% in 1 hour, about 60% to about 75% in 2 hours, and at least about 90% in 4 hours by adjusting the % hydroxypropoxylated.

The present disclosure yet further provides a series of three dosage forms that in conjunction with existing dosage forms minimizes the guesswork on the part of a prescriber in providing the proper dosing or strength for a patient.

Further according to the present disclosure, there is provided a method of assisting a physician in prescribing a dose of minocycline for the treatment of acne. The method has the steps of (a) determining the body weight of a patient preferably by weighing the patient; (b) referring to a chart or reference tool that correlates a plurality of body weight ranges with a corresponding number of dosage forms each having a different level of minocycline based on a target dosage rate of about 1 mg/kg/day; (c) identifying a single dosage form corresponding to the weight of the patient in the chart or reference tool; and (d) administering to the patient the identified single dosage form. The identified single dosage form includes an amount of minocycline selected from the group consisting of 55 mg, 80 mg, and 105 mg.

DETAILED DESCRIPTION OF THE DISCLOSURE

The present disclosure relates to three oral dosage forms or strengths having different amounts or levels of minocycline: 55 mg, 80 mg, and 105 mg. The three dosage forms, are preferably tablets, and allow physician versatility in precisely prescribing an oral dosage that will most closely provide for the desirable 1 mg/kg/day body of minocycline in a patient.

It was surprisingly found in the present disclosure that hydroxypropylmethylcellulose (HPMC) could be selected based upon hydroxypropyl (HP) content at least 8.3 to about 9.8% (% hydroxypropoxylated or % HP) on a molar basis to provide a desired release profile that substantially reduces the likelihood of side effects. The 55 mg, 80 mg, and 105 mg strengths further reduce the dosing variation among users at the different weight groups. The dosing options track within a range the recommended dose of 1 mg/kg/day for several common patient weight ranges.

Each dosage strength includes minocycline, preferably minocycline hydrochloride, in a dissolution rate controlling matrix polymer, which optimizes the temporal release from the dosage strength to deliver therapeutic amounts, when orally administered. Each dosage strength provides a therapeutic dosage strength of minocycline incorporated therein. The dosage strengths are calculated based on the therapeutic concentrations required per day; on the basis of patient/person weight, which concentrations amount to about 1 mg/kg/day. The dissolution profiles at the 55 mg, 80 mg, and 105 mg dosage strengths corroborate that therapeutic levels of the minocycline can be provided in vivo. Each dosage strength provides, without an initial load dose, a relatively if not completely constant, slow, continuous release of the minocycline from the dosage strength in the patient so that steady-state equilibrium is maintained using QD (once-a-day) dosing. This is evident from the in vitro dissolution data in an aqueous medium of pH 1.2 in Tables 5 to 8, which demonstrate a desirable, constant release rate of the minocycline about 35% to about 50% in 1 hour, about 60% to about 75% in 2 hours, and at least about 90% in 4 hours after oral administration.

Since body weight varies among patients, it is not practical to provide every patient with exactly 1 mg/kg/day of minocycline. However, it is acceptable to approximate this dose by providing the patient with about 1 mg/kg/day. For purposes of the present disclosure with respect to the 55 mg, 80 mg and 105 mg dosages, "about 1 mg/kg of body weight per day" means from 0.93 mg/kg/day to 1.11 mg/kg/day. A correlation between patient weight and tablet strength is shown by way of example in Table 1 below.

TABLE 1

(Tablet Dosing Table)

| | Ranges | | |
|---|---|---|---|
| Strength | Patient's Weight (lbs) | Patient's Weight (kg) | Actual mg/kg Dose |
| 55 mg | 110-131 | 50-59 | 1.1-0.93 |
| 80 mg | 158-186 | 72-84 | 1.11-0.95 |
| 105 mg | 213-243 | 97-110 | 1.08-0.95 |

Since the number of dosage strengths that can reasonably be manufactured and commercially distributed is relatively small, dosage strengths must be appropriately selected in view of projected patient weights to provide the desirable 1 mg/kg/day minocycline dosage rate within an efficacious range.

The dosage forms or strengths are to be orally administered once per day to patients in need of treatment for acne. A conventional useful treatment regimen is 12 weeks, but longer and shorter regimens are also possible. In other embodiments, regimens of two weeks or more and three weeks or more are possible.

The weight of minocycline hydrochloride in the dosage forms as used herein is the free base weight of minocycline. The form of minocycline employed herein, minocycline hydrochloride, is referenced with respect to the weight of its free base. Thus, the strengths of minocycline hydrochloride in the present dosage forms, 55 mg, 80 mg, and 105 mg, are based on the free base weight of minocycline.

The dosage forms have a vehicle. The preferred vehicle has a fast dissolving carrier and a slow dissolving carrier. The slow dissolving carrier is an amount of hydroxypropylmethylcellulose (HPMC) that is at least 8.3% to about 9.8% hydroxypropoxylated (HP) on a molar basis. It was surprisingly found in the present disclosure that HPMC could be selected based on the % HP to provide the desired extended release profile for minocycline hydrochloride. The HPMC dissolves slowly over the course of hours. For HPMC having less than 8.3% HP, the dissolution rate is believed to be too slow to achieve the desired dissolution profile. For HPMC having greater than 9.8% HP, the dissolution rate is believed to be too fast to achieve the desired dissolution profile. A preferred range of hydroxypropylation is 8.3% to about 9.1%. Desired dissolution profiles have been observed for dosage forms using HPMC having about 8.9 to 9.1 HP. It is envisioned that the desired dissolution profile can also be achieved using HPMC having 8.3% to about 9.1% HP. The HPMC also functions as a binder and release rate controlling agent and preferably exhibits a viscosity in water of between 40 and 60 cP and most preferably 50 cP according to ASTM E2503-07.

The vehicle includes a fast dissolving carrier. In the intended commercial dosage forms, the fast dissolving carrier has an intragranular fast dissolving carrier component and an extragranular fast dissolving carrier component. Preferably, the fast dissolving carrier is lactose monohydrate. The lactose monohydrate, or preferred fast dissolving carrier, quickly dissolves in an aqueous physiological medium, such as gastric fluid.

In a preferred embodiment, the HPMC level is the same for all three dosage forms of minocycline, while the lactose monohydrate is adjusted depending the amount of minocycline in order to maintain a dosage form or tablet weight at 400 mg. The dosage forms weights refer to uncoated tablet or cores and do not include the weight of any coatings.

It is advantageous for certain embodiments of the present disclosure to formulate the dosage forms so that the weight ratio of the extragranular fast dissolving carrier to intragranular slow dissolving carrier is from 0.30 to 0.50, preferably from 0.35 to 0.45, and most preferably 0.36 to 0.40

In a preferred embodiment for making the tablets, minocycline hydrochloride is blended and granulated with a mixture of lactose monohydrate (intragranular) and HPMC (intragranular). The granules are then blended with additional lactose monohydrate (extragranular), colloidal silicon dioxide and magnesium stearate to form a mixture that is compressed to form tablets. The tablets are then optionally spray-coated to form coated tablets. Coated tablets are preferred.

Preferred tablet coatings are film-forming polymers. Useful coating polymers include methyl cellulose, ethylcellulose, hydroxyethyl cellulose, hydroxypropyl cellulose, hydroxypropyl methylcellulose (HPMC), hydroxypropyl methylcellulose phthalate, cellulose acetate phthalate, hydroxypropyl methylcellulose succinate, polymers and copolymers of (meth)acrylic acid or (meth)acrylic acid methyl ester, polyvinyl acetate phthalate or polymers or copolymers of polyvinyl acetate, cellulose acetate, fatty acids and esters thereof, cellulose acetate trimellitate, and any combinations of the foregoing. The coating can substantially completely dissolve in a medium having a pH of less than about 3.9, such as found in the stomach and gastrointestinal tract. The coating can also optionally include conventional additives, such as a plasticizer, a pigment, and a colorant. The plasticizers include a mineral oil, a high boiling ester, and a vegetable oil. Preferred coatings are those containing Opadry polymers (Colorcon Inc.). A coating may take the form of a single coating or multiple coatings. Carnauba wax is subsequently optionally added to the coated tablets as a polishing agent.

The present disclosure is useful in assisting a physician in prescribing a dose of minocycline for the treatment of acne. The physician or prescriber weighs a patient or asks the patient his or her body weight. The physician or prescriber then refers to a chart or reference tool that correlates a plurality of body weight ranges with a corresponding number of dosage forms each having a different level of minocycline based on a target dosage rate of about 1 mg/kg/day. The physician or prescriber then identifies a single dosage form corresponding to a particular weight range in which the patient's weight falls in the chart or reference tool. The physician or prescriber then administers to the patient or otherwise prescribes the identified single dosage form, which correspond to the dosage forms or tablets disclosed in the present disclosure. In the preferred embodiment disclosed herein, three discrete weight ranges are correlated with the three discrete strengths of dosage forms or tablets.

A chart useful in assisting a physician or prescriber, for example, can take a form similar to Table 1 herein. Other reference tools can take the form of conventional medical diagnostic tools, such as ruler/stick aligning device, circular aligning device, computer program, and the like.

The dosage form or tablet of the present disclosure can be administered with little or substantially no side effects compared to a placebo. Vestibular side effects that are substantially avoided include: headache, fatigue, dizziness, drowsiness, pruritus, lightheadedness, malaise, mood alteration, somnolence, urticaria, tinnitus, arthralgia, vertigo, dry mouth, and myalgia. Other adverse effects that can be avoided include blood/lymphatic system, ear and labyrinth, endocrine, eye, gastrointestinal, immune system, syncope, contusions, vaginal itching, nausea, nasal congestion, cough, itch, rash, stomach pain, infections, infestations, laboratory blood abnormalities, metabolism, nutrition, musculoskeletal and connective neoplasms, benign, malignant and unspecified nervous system psychiatric, renal and urinary, reproductive system, breast disorders, respiratory, thoracic and mediastinal, skin and subcutaneous tissue, and vascular.

It is envisioned to make oral dosage forms, e.g., tablets, having levels of minocycline hydrochloride and using the % HP to maintain levels of the desired release or dissolution rates for dosage forms other than 55 mg, 80 mg, and 105 mg. For instance, oral dosage forms having minocycline hydrochloride levels of 45 mg, 65 mg, 90 mg and 115 mg are possible. These other dosage forms can be made in a manner similar to that described elsewhere herein with the % HP at least about 8.3% to about 9.8% so that the oral dosage form maintains the desired dissolution profile or release rates about 35% to about 50% in 1 hour, about 60% to about 75% in 2 hours, and at least about 90% in 4 hours, while providing a daily dose of 1 mg/kg (about 1.1 mg/kg to about 0.9 mg/kg) of body weight.

The following are examples of the present disclosure and are not to be construed as limiting.

EXAMPLES

These film-coated tablets according to the present disclosure were manufactured and tested for dissolution rate. The film-coated tablets contain minocycline hydrochloride, equivalent to minocycline as an active drug substance. The three tablets are preferably color coded for easy identification.

Qualitative and quantitative properties of examples of the tablets are set forth in Tables 2 and 3 below. Processes for making the tablets, including preparation of tablet composition, compression, and tablet coating, are set forth below in Table 4.

All three tablets have the same unit weight, and, thus, different ratios of active to inactive ingredients. All three strengths have the same ratio of HPMC (hypromellose), the release-controlling excipient, to unit weight compared to the tablets having less minocycline. The three tablets differ from each other only in the amount of minocycline, lactose monohydrate, and the color of the coating material.

TABLE 2

(Examples of Qualitative Tablet Compositions)

Core Tablet

| Component | Quality Standard | Function |
|---|---|---|
| Minocycline Hydrochloride CAS 13614-98-7 | USP | Active |
| Lactose Monohydrate (Fast-Flo 316) CAS 000063423 | NF | Filler |
| Hypromellose, Type 2910 (Methocel ® E50 Premium LV) CAS 009004653 | USP | Binder/Release Rate Controlling Polymer |
| Colloidal Silicon Dioxide (Cab-o-Sil M-5) CAS 00631869 | NF | Glidant |
| Magnesium Stearate (Impalpable Powder) (FCC HyQual ® Product Code 2255) CAS 000557040 | NF | Lubricant |
| Powdered Refined Carnauba Wax #20 CAS 008015869 | NF | Polishing Agent |
| Purified Water | USP | Processing Aid |

Film Coating Suspension

| Component | Quality Standard | Tablet Strength |
|---|---|---|
| Opadry II Pink (33G94514) | | 55 mg |
| Opadry II Gray (33G97580) | | 80 mg |
| Opadry II Purple (33G10146) | | 105 mg |
| Purified Water | USP | All strengths |

CAS = Chemical Abstract Registry Number

TABLE 3

(Examples of Quantitative Tablet Composition)

| Component | Reference to Quality Standard | Amount (mg) per Tablet | | |
|---|---|---|---|---|
| | | 55 mg | 80 mg | 105 mg |
| Minocycline Hydrochloride§ | USP | 55. | 80 | 105 |
| Lactose Monohydrate ( #316 Fast Flo) - \Intragranular | NF | 187 | 162 | 137 |
| Lactose Monohydrate ( #316 Fast Flo) - Extragranular | NF | 41 | 41 | 41 |
| Hypromellose, Type 2910 (Methocel ™ E50 Premium LV) | USP | 108 | 108 | 108 |
| Colloidal Silicon Dioxide (Cab-o-Sil M-5) | NF | 3 | 3 | 3 |

TABLE 3-continued (Examples of Quantitative Tablet Composition)

|  | Reference to Quality | Amount (mg) per Tablet | | |
|---|---|---|---|---|
| Component | Standard | 55 mg | 80 mg | 105 mg |
| Magnesium Stearate (Impalpable Powder) | NF | 6 | 6 | 6 |
| Core Tablet Weight |  | 400 | 400 | 400 |
| Film Coating Suspension | | | | |
| Opadry II Pink 33G94514[#] | Supplier standard | 14 | | |
| Opadry II Gray 33G97580[#] | Supplier standard | | 14 | |
| Opadry II Purple 33G10146[*] | Supplier standard | | | 12.4 |
| Purified Water[#] | USP | N/A | N/A | N/A |
| Carnauba Wax | NF | N/A | N/A | N/A |
| Total Tablet Weight |  | 414 | 414 | 412.4 |

[§]The amount of minocycline hydrochloride calculated is based on the assay and moisture content from the manufacturer's certificate of analysis.
[#]The theoretical amount of Opadry II and Purified Water dispensed represents a 50% excess of the theoretical amount required to achieve a 3.5% weight gain on the theoretical batch size.
[*]The theoretical amount of Opadry II Purple dispensed represents a 69% excess of the theoretical amount required to achieve a 3.1% weight gain on the theoretical batch size.

TABLE 4

(Methods for the Making the Tablets)

| | Strength | | |
|---|---|---|---|
| Quantity/dosage form | 55 mg mg/dose | 80 mg mg/dose | 105 mg mg/dose |
| Intragranular Component | | | |
| Dry Blend Parameters: | | | |
| Screening of intragranular Lactose Monohydrate: | | | |
| Spacer: | 0.150" | 0.150" | 0.150" |
| Screen | 2C075R050/51 | 2C075R050/51 | 2C075R050/51 |
| Impeller | 2C1601 | 2C1601 | 2C1601 |
| Speed: | approx. 875 rpm | approx. 875 rpm | approx. 875 rpm |
| Impeller Seal Pressure | 10 +/− 5 psi | 10 +/− 5 psi | 10 +/− 5 psi |
| Chopper Seal Pressure | 10 +/− 5 psi | 10 +/− 5 psi | 10 +/− 5 psi |
| Mixing Time | 2 minutes +/− 10 sec. | 2 minutes +/− 10 sec. | 2 minutes +/− 10 sec. |
| Blender Speed | Speed #1 | Speed #1 | Speed #1 |
| Granulator Speed | OFF | OFF | OFF |
| Granulation Parameters: | | | |
| Granulation Spray Rate | 7,500 g/min +/− 500 g/min | | |
| Granulation Time | 7 min. 34 sec +/− 30 seconds | | |
| Blender Speed | Speed #1 | Speed #1 | Speed #1 |
| Granulator Speed | Speed #1 | Speed #1 | Speed #1 |
| Nozzle | ¼ VVS9520 | ¼ VVS9520 | ¼ VVS9520 |
| Wet Massing Parameters | | | |
| Mixing Time | 3 minutes +/− 30 seconds | | |
| Blender Speed | Speed #1 | Speed #1 | Speed #1 |
| Granulator Speed | Speed #1 | Speed #1 | Speed #1 |
| Wet Milling Parameters | | | |
| Spacer: | 0.150" | 0.150" | 0.150" |
| Speed: | approx. 900 rpm | approx. 900 rpm | approx. 900 rpm |
| Blender Speed | Speed #1 | Speed #1 | Speed #1 |
| Granulator Speed | OFF | OFF | OFF |
| Screen | 2F250Q037/50 | 2F250Q037/50 | 2F250Q037/50 |
| Impeller | 2C1607 | 2C1607 | 2C1607 |
| Spacer: | 0.150" | 0.150" | 0.150" |
| Fluid Bed Drying Parameters | | | |
| Pre-heat Parameters - | | | |
| Fluid Bed Dryer | | | |
| Process Air Volume Set Point | 500-1000 cfm | 500-1000 cfm | 500-1000 cfm |
| Inlet Air Temperature | 65° C. (60° C.-70° C.) | 65° C. (60° C.-70° C.) | 65° C. (60° C.-70° C.) |
| Time | At least 15 min. | At least 15 min. | At least 15 min. |
| Fluid Bed Drying Parameters | | | |
| Initial Process Air Volume Set Point | 1200 cfm | 1200 cfm | 1200 cfm |
| Process Air Volume Set Point Range | 500-2500 cfm | 500-2500 cfm | 500-2500 cfm |
| Inlet Air Temperature | 65° C. | 65° C. | 65° C. |

TABLE 4-continued (Methods for the Making the Tablets)

| | Strength | | |
|---|---|---|---|
| Quantity/dosage form | 55 mg mg/dose | 80 mg mg/dose | 105 mg mg/dose |
| Set Point Range | (60° C.-70° C.) | (60° C.-70° C.) | (60° C.-70° C.) |
| Shake Type | WSG mode | WSG mode | WSG mode |
| Shake Interval | 30 seconds | 30 seconds | 30 seconds |
| Shake Duration | 5 seconds | 5 seconds | 5 seconds |
| Target LOD | Target 1.7% (1.1-2.1%) | Target 1.9% (1.3-2.3%) | Target 2.2% (1.7-2.7%) |
| Dry Sizing Parameters | | | |
| Feed Screw Speed | 14-16 rpm | 14-16 rpm | 14-16 rpm |
| Rotor Speed | 4600 +/− 25 rpm | 4600 +/− 25 rpm | 4600 +/− 25 rpm |
| Screen | 1532-0050 | 1532-0050 | 1532-0050 |
| Knives | Forward | Forward | Forward |
| Extragranular Component | | | |
| Excipient Blending/Milling Parameters: | | | |
| Adjusted Colloidal Silicon Dioxide, NF + | | | |
| Extragranular Lactose form Extragranular Blend | | | |
| 3 cu. Ft. V-Blender Speed: | 2 minutes +/− 15 seconds | | |
| Spacer: | 0.150" | 0.150" | 0.150" |
| Speed: | approx. 875 rpm | approx. 875 rpm | approx. 875 rpm |
| Screen | 2C075R050/51 | 2C075R050/51 | 2C075R050/51 |
| Impeller | 2C1601 | 2C1601 | 2C1601 |
| Blending of the Intragranular and Extragranular Blends | | | |
| Bin Speed | 15 rpm | 15 rpm | 15 rpm |
| Bin Blend Time | 10 minutes +/− 15 sec | 10 minutes +/− 15 sec | 10 minutes +/− 15 sec |
| Adjusted Magnesium Stearate + 5 kg Blend | | | |
| 1 cu. Ft. V-Blender Speed: | 2 minutes +/− 15 seconds | 2 minutes +/− 15 seconds | 2 minutes +/− 15 seconds |
| Spacer: | 0.150" | 0.150" | 0.150" |
| Speed: | approx. 875 rpm | approx. 875 rpm | approx. 875 rpm |
| Screen | 2C075R050/51 | 2C075R050/51 | 2C075R050/51 |
| Impeller | 2C1601 | 2C1601 | 2C1601 |
| Final Blend Parameters | | | |
| Bin Speed | 15 rpm | 15 rpm | 15 rpm |
| Bin Blend Time | 10 minutes +/− 15 sec | 10 minutes +/− 15 sec | 10 minutes +/− 15 sec |
| Compression Parameters | | | |
| Size: | 0.2343 × 0.6250" | 0.2343 × 0.6250" | 0.2343 × 0.6250" |
| Tablet Weight | 400 mg | 400 mg | 400 mg |
| Acceptance Criteria | 390 mg-410 mg (97.5-102.5%) | | |
| Tablet Hardness | 10 tablets/30 minutes | 10 tablets/30 minutes | 10 tablets/30 minutes |
| Average Hardness Target | 15 kp | 15 kp | 15 kp |
| Individual Hardness Range | 12-18 kp | 12-18 kp | 12-18 kp |
| Tablet Thickness Range | 5 tablets/30 minutes | 5 tablets/30 minutes | |
| Tablet Thickness Target | 4.52 mm | 4.52 mm | 4.52 mm |
| Friability | No more than 1% after 4 min. | No more than 1% after 4 min. | No more than 1% after 4 min. |
| Coating Suspension Mixing Parameters | | | |
| Mixing Time | NLT 60 minutes | NLT 60 minutes | NLT 60 minutes |
| Screen Coating Suspension | 80 mesh ss screen | 80 mesh ss screen | 80 mesh ss screen |
| Prior to Use | | | |
| Coating Parameters | | | |
| % weight gain - Target | 3.85% wet | 3.85% wet | 3.3% wet |
| % weight gain - Range | 3.0-4.0% | 3.0-4.0% | 3.0-3.3% |
| Supply Temperature | Preheat 47° C. | Preheat 47° C. | Preheat 47° C. |
| | (Range 45° C.-50° C.) | (Range 45° C.-50° C.) | (Range 45° C.-50° C.) |
| | Spraying 62° C. | Spraying 62° C. | Spraying 62° C. |
| | (range 60° C.-70° C.) | (range 60-70° C.) | (range 60-70° C.) |
| Distance From Spray Tips to Tablet Bed | 20-25 cm | 20-25 cm | 20-25 cm |
| Atomizing Air Pressure | 30 psi +/− 10 psi | 30 psi +/− 10 psi | 30 psi +/− 10 psi |
| Pattern Air Pressure | 30 psi +/− 10 psi | 30 psi +/− 10 psi | 30 psi +/− 10 psi |
| Flow Rate | 400 g/min +/− 100 g/min | 400 g/min +/− 100 g/min | 400 g/min +/− 100 g/min |
| | (100 g/min +/− 25 g/min per gun) | (100 g/min +/− 25 g/min per gun) | (100 g/min +/− 25 g/min per gun) |
| Pan Pressure | −0.1--0.2 inches of water | −0.1--0.2 inches of water | −0.1--0.2 inches of water |
| Pan Speed During Coating | 7 +/− 2 rpm | 7 +/− 2 rpm | 7 +/− 2 rpm |
| Pan Speed During Polishing | 7 +/− 2 rpm | 7 +/− 2 rpm | 7 +/− 2 rpm |
| Pan Speed During Tumbling | 4 +/− 1 rpm | 4 +/− 1 rpm | 4 |
| Air Volume | 2000 cfm +/− 200 cfm | 2000 cfm +/− 200 cfm | 2000 cfm +/− 200 cfm |
| Number of Spray Guns | 4 | 4 | 4 |

TABLE 4-continued (Methods for the Making the Tablets)

| | Strength | | |
|---|---|---|---|
| Quantity/dosage form | 55 mg mg/dose | 80 mg mg/dose | 105 mg mg/dose |
| Post spraying parameters(drying) | | | |
| Pan Speed | 1 rpm | 1 rpm | 1 rpm |
| Supply Air Temperature | cool to <35° C. | cool to <35° C. | cool to <35° C. |
| Addition of Carnauba Wax | | | |
| Pan Speed | 7 rpm | 7 rpm | 7 rpm |
| Tumble Time | 2 min | 2 min | 2 min |

Residual Moisture Content

During the drying of the wet granulation, samples are taken and subjected to destructive testing that determines the amount of residual moisture content remaining by means of Loss on Drying (LOD). The target LODs for the different strengths are:

55 mg: target 1.7% with a range of 1.1% to 2.1%
80 mg: target 1.9% with a range of 1.3% to 2.3%
105 mg: target 2.1% with a range of 1.7% to 2.7%

The primary critical in-process test is blend uniformity. Blend sampling of the final blend occurs in the blender where samples are taken from 10 locations. Sample sizes are 1 to 3 times the target core tablet weight of 400 mg, i.e., 0.4 grams to 1.2 grams. Sample locations are top left, top center, top right, middle left edge, middle left third, middle right third, middle right edge, bottom left, bottom center and bottom right. These locations are also location indicators of the blender where the sample was taken with a thief.

Samples are submitted for analysis. Results include the % label claim, the mean % label claim and the relative standard deviation of the 10 samples. If results are acceptable, i.e., mean % label claim of 90%-110% and relative standard deviation <6.0%.

During the compression of the final blend, tablet samples are taken from the beginning, middle and end of the run and friability is determined using a standard friabilator, as described in the United States Pharmacopeia. The sample size is 17 tablets.

At predetermined intervals during the compression run, samples of tablets are taken and subjected to destructive testing. For 10 individual tablets, the weight, thickness and hardness are determined. Samples are typically taken every 15 minutes during the compression run.

Coating of Tablets

The cores are divided into two equal parts for two pan loads. A calculation is performed to determine the quantity of coating solution required for each pan. The cores are then heated in the coating pan and after the cores reach temperature, a sample of 50 tablets are taken to determine the average core weight after heating. This weight is then multiplied by the desired % weight gain. This value is used as the theoretical end point of the coating operation. After approximately 15 kg of coating, average weight samples are taken every 10 minutes until the desired wet % weight gain has been achieved. Once this value is achieved, the tablets are dried for 2-5 minutes. At the completion of the drying phase, a sample of 50 tablets are removed and weighed for a final average tablet weight. If the average tablet weight is within specification, the tablets are cooled to less than 35° C. When this temperature is achieved, the wax is applied to the tablets.

Dissolution Testing

The three tablets were tested for dissolution in a paddle test apparatus at 0.1 HCl and a pH of 1.2 according to ASTM E2503-07. The results are set forth below in Tables 7 to 9.

TABLE 7

(Net Effect on 55 mg Minocycline Tablet using HPMC with a 8.9% to 9.1% HP on dissolution profile)

| | Dissolution Specification (% dissolved) | | |
|---|---|---|---|
| | 35-50% | 60-75% | NLT 90% |
| Time Point | 1 hour | 2 hour | 4 hour |
| Supplement Batches Dissolution Results - 8.9-9.1% HP HPMC | 41.8 | 70.8 | 99.7 |

NLT—not less than

TABLE 8

(Net Effect on 80 mg Minocycline Tablet using HPMC with a 8.9% to 9.1% HP on dissolution profile)

| | Dissolution Specification | | |
|---|---|---|---|
| | 35-50% | 60-75% | NLT 90% |
| Time Point | 1 hour | 2 hour | 4 hour |
| Supplement Batches Dissolution Results at 8.9-9.1% HP HPMC | 41.6 | 71.3 | 100.4 |

TABLE 9

(Net Effect on 105 mg Minocycline Tablet using HPMC with 8.9% to 9.1% HP on dissolution profile)

| | Dissolution Specification | | |
|---|---|---|---|
| | 35-50% | 60-75% | NLT 90% |
| Time Point | 1 hour | 2 hour | 4 hour |
| Supplement Batches Dissolution Results at 8.9-9.1% HPMC | 40.4 | 70.9 | 99.6 |

Tables 10A to 10C show the net effect of using HMPC with 8.3 to 9.8% HP in the manufacture of 55, 80, 90, and 105 mg extended-release (ER) minocycline tablets. The 90 mg tablets were prepared in a manner similar to those of 55, 80, and 105 mg except that the amount of intragranular lactose monohydrate was modified to yield a core tablet weight of 400 mg. The core tablet was subsequently coated with 14 mg of Opadry II 33G12224 and polished with a trace amount of carnauba wax. The dissolution tests for the 55, 80, and 105 mg (ER) tablets correspond to those previously set forth in Tables 7 to 9.

TABLE 10A

| | Dissolution Specification | | | |
|---|---|---|---|---|
| | 35-50% | 60-75% | NLT 90% | % HP |
| Time Point | 1 hour | 2 hour | 4 hour | |
| Minocycline ER 55 mg 8.9-9.1% HP HPMC | 41.8 | 70.8 | 99.7 | 8.9-9.1% |
| Minocycline ER 90 mg 8.3% HP HPMC | 37 | 62.8 | 98.6 | 8.3% |
| Minocycline ER 90 mg 9.8% HP HPMC | 43 | 73 | 102 | 9.8% |

TABLE 10B

| | Dissolution Specification | | | |
|---|---|---|---|---|
| | 35-50% | 60-75% | NLT 90% | % HP |
| Time Point | 1 hour | 2 hour | 4 hour | |
| Minocycline ER 80 mg 8.9-9.1% HP HPMC | 41.6 | 71.3 | 100.4 | 8.9-9.1% |
| Minocycline ER 90 mg 8.3% HP HPMC | 37 | 62.8 | 98.6 | 8.3% |
| Minocycline ER 90 mg 9.8% HP HPMC | 43 | 73 | 102 | 9.8% |

TABLE 10C

| | Dissolution Specification | | | |
|---|---|---|---|---|
| | 35-50% | 60-75% | NLT 90% | % HP |
| Time Point | 1 hour | 2 hour | 4 hour | |
| Minocycline ER105 mg 8.9-9.1% HP HPMC | 40.4 | 70.9 | 99.6 | 8.9-9.1% |
| Minocycline ER 90 mg 8.3% HP HPMC | 37 | 62.8 | 98.6 | 8.3% |
| Minocycline ER 90 mg 9.8% HP HPMC | 43 | 73 | 102 | 9.8% |

The results in Tables 10A-C showed that each of the tablets achieved dissolution within the dissolution specification corresponding to each of the time points of 1 hour, 2 hours and 4 hours. The results in Tables 10A-C also showed that increased dissolution can be achieved at each of 1 hour, 2 hours and 4 hours when the HP % is increased from 8.3% to 9.8%. The increase in dissolution at the two-hour time point was particularly great.

Other ER 90 minocycline hydrochloride mg tablets of varying HP % were tested for dissolution level at the 1 and 2 hours. At HP % levels of about 8.7% to about 9%, a ramping (significant increase) of dissolution levels of from about 40 to about 42% at the one-hour time point and 65% to about 72% at the two-hour time point was observed. The data indicated that selection of HP % within this range or around it may be useful in controlling dissolution level at the one- and two-hour time points. The data also indicated that high dissolution levels can be achieved within this HP % range.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances that fall within the scope of the appended claims.

What is claimed is:

1. A method of treating acne in a human, comprising: administering to the human once per day an oral dosing form including:
   an amount of minocycline selected from the group consisting of 55 mg, 80 mg, and 105 mg;
   an amount of lactose monohydrate; and
   an amount of hydroxypropylmethylcellulose,
   wherein the hydroxypropylmethylcellulose is at least 8.3 to about 9.8% hydroxypropoxylated; and wherein the minocycline in the oral dosage form has a dissolution of about 35% to about 50% in 1 hour, about 60% to about 75% in 2 hours, and at least about 90% in 4 hours.

2. The method of claim 1, wherein the oral dosage form provides the patient with an amount of minocycline at about 1.1 mg/kg to about 0.9 mg/kg of body weight.

3. The method of claim 2, wherein the oral dosage form provides the patient with an amount of minocycline at 1 mg/kg of body weight.

4. The method of claim 1, wherein the hydroxypropylmethylcellulose is 8.3 to about 9.1% hydroxypropoxylated.

5. The method of claim 4, wherein the hydroxypropylmethylcellulose is 8.9 to 9.1% hydroxypropoxylated.

6. The method of claim 1, wherein the lactose monohydrate is present in an intragranular component and in an extragranular component.

7. A method of assisting a physician in prescribing a dose of minocycline for the treatment of acne, comprising:
   (a) determining the body weight of a patient;
   (b) referring to a chart or reference tool that correlates a plurality of body weight ranges with a corresponding number of dosage forms each having a different level of minocycline based on a target dosage rate of 1 mg/kg/day;
   (c) identifying a single dosage form corresponding to a particular weight range in which the patient's weight falls in the chart or reference tool; and
   (d) administering to the patient the identified single dosage form, wherein the identified single dosage form includes:
   an amount of minocycline selected from the group consisting of 55 mg, 80 mg, and 105 mg,
   an amount of lactose monohydrate, and
   an amount of hydroxypropylmethylcellulose, wherein the hydroxypropylmethylcellulose is at least 8.3 to about 9.8% hydroxypropoxylated, and wherein the minocycline in the oral dosage form has a dissolution of about 35% to about 50% in 1 hour, about 60% to about 75% in 2 hours, and at least about 90% in 4 hours.

8. The method of claim 7, wherein the hydroxypropylmethylcellulose is 8.3 to about 9.1% hydroxypropoxylated.

9. The method of claim 8, wherein the hydroxypropylmethylcellulose is 8.9 to 9.1% hydroxypropoxylated.

10. The method of claim 7, wherein the lactose monohydrate is present in an intragranular component and an extragranular component.

* * * * *